(12) United States Patent
Oide et al.

(10) Patent No.: US 7,228,999 B2
(45) Date of Patent: Jun. 12, 2007

(54) CLINCHER FOR STAPLER

(75) Inventors: Ikuo Oide, Tokyo (JP); Yutaka Oshima, Tokyo (JP)

(73) Assignee: Max Co., Ltd., Tokyo (JP)

( * ) Notice: Subject to any disclaimer, the term of this patent is extended or adjusted under 35 U.S.C. 154(b) by 70 days.

(21) Appl. No.: 10/532,964

(22) PCT Filed: Mar. 10, 2004

(86) PCT No.: PCT/JP2004/003056

§ 371 (c)(1),
(2), (4) Date: Apr. 27, 2005

(87) PCT Pub. No.: WO2004/082896

PCT Pub. Date: Sep. 30, 2004

(65) Prior Publication Data

US 2006/0043146 A1    Mar. 2, 2006

(30) Foreign Application Priority Data

Mar. 18, 2003   (JP) .............................. 2003-073209

(51) Int. Cl.
*B25C 5/02*   (2006.01)
(52) U.S. Cl. ...................................... 227/155; 227/119
(58) Field of Classification Search ................ 227/155, 227/119, 134, 154, 131
See application file for complete search history.

(56) References Cited

U.S. PATENT DOCUMENTS

| 2,320,703 | A | * | 6/1943  | Maynard ...................... 227/99  |
| 3,871,227 | A | * | 3/1975  | Tidwell, Jr. .................. 72/476 |
| 4,281,785 | A | * | 8/1981  | Brooks ........................ 227/120 |
| 4,632,290 | A | * | 12/1986 | Green et al. .................. 227/19  |
| 5,413,266 | A | * | 5/1995  | Jairam ......................... 227/129 |
| 5,480,089 | A | * | 1/1996  | Blewett ................... 227/175.1 |
| 6,592,115 | B2 | * | 7/2003  | Yamaguchi .............. 270/58.08 |
| 6,925,849 | B2 | * | 8/2005  | Jairam ......................... 72/476  |

FOREIGN PATENT DOCUMENTS

| JP |   63-150169 |    | 6/1988 |
| JP |    6-7893 | Y2 | 3/1994 |

* cited by examiner

*Primary Examiner*—Scott A. Smith
(74) *Attorney, Agent, or Firm*—Morgan, Lewis & Bockius LLP

(57) ABSTRACT

In a clincher device 1, 11 of a stapler adapted to be engaged with staple legs S1 which have been ejected from a driver unit by a driver 10 toward sheets of paper and have penetrated through the sheets of paper, thereby to clinch the staple legs S1 on a back face side of the sheets of paper, a plurality of projected lines 8, 9, 14 to be engaged with the staple legs S1 are provided in parallel with one another, on faces of the clincher device 1, 11 for guiding the staple legs inwardly.

5 Claims, 9 Drawing Sheets

CLINCHER FOR STAPLER

TECHNICAL FIELD

The present invention relates to a clincher device of a stapler for guiding a leg of a staple penetrated through sheets of paper by an engagement of the leg of the staple and a clincher, and clinching the leg along a back face of the sheets of paper.

BACKGROUND ART

Generally, a stapler comprises a driver unit which contains a number of staples and ejects a C-shaped staple toward sheets of paper by a driver, and a clincher unit which is opposed to the driver unit and clinches tip end of the leg of the staple penetrated through the sheets of paper along a back face of the sheets of paper. The staple is ejected from the driver unit toward the sheets of paper placed between the two units, and a clincher device of the clincher unit engages with the tip end of the leg of the staple penetrated through the sheets of paper to inwardly bend the leg so as to clinch the leg along the back face of the sheets of paper.

It is required that the driver unit and the clincher unit are positioned in accurate alignment so that a leading end of the staple ejected from the driver unit can be accurately engaged with the clincher device of the clincher unit. However, in the stapler mounted in a copying machine or the like, the driver unit and the clincher unit are constructed separately, and the two units are independently controlled so as to move in a sliding direction and in a rotary direction in order that the sheets of paper after copied can be bound at a desired position. Because the stapler is so constructed that the two units can move in this manner, a positional deviation may occur between the staple ejected from the driver unit and the clincher device of the clincher unit, and so, the leg of the staple ejected from the driver unit may not be engaged with the clincher device of the clincher unit, which will cause a binding error. Therefore, there has been such a problem that it takes a long time to adjust positioning of the two units.

Moreover, the conventional clincher device of the stapler is so constructed that a receiving face for the leg of the staple is wide, and stationary walls are provided so as to be opposed to each other on both sides of a clincher member with clinching groove having a substantially same width as the staple. In the stationary walls, an inclined face for guiding the tip end of the leg of the staple which have penetrated through the sheets of paper into the clinching groove of the clincher member is formed, and the tip end of the leg of the staple which have penetrated through the sheets of paper is guided into the clinching groove of the clincher member along the inclined face (Refer to JP-Y-06-007893, for example).

As shown in FIG. 8, since the receiving face is formed wide in the above conventional clincher device 20, leg portion S1 of a staple S can be engaged with the clincher device 20, even in case where a slight deviation has occurred between the clincher unit and the driver unit. However, since the staple leg S1 is guided into clinching groove 23 of a clincher member 22 along inclined face 21, when a tip end S2 of the staple leg S1 penetrated through sheets of paper is inwardly bent by the clincher member 22, the staple S will be inclined and fallen down while the tip end S2 of the staple leg S1 is guided in a longitudinal direction by the inclined face 21. As the results, such a phenomenon that the sheets of paper is bound in a state where both the legs S1 are not in parallel with a crown part of the staple but inclined, as shown in FIG. 9, may occur. In case where the staple S having the long leg S1 is used, it may sometimes happen that both the legs S1 are crossed.

DISCLOSURE OF THE INVENTION

The invention has been made to solve the problems in the prior art as above, and an object of the invention is to provide a clincher device of a stapler which can clinch both legs of a staple along a back face of sheets of paper, so as to be in parallel with a crown part, even in case where a driver unit for ejecting the staple and a clincher unit for clinching the staple legs are deviated in position from each other.

In order to solve the above problems, there is provided according to the invention, a clincher device of a stapler which is adapted to be engaged with staple leg which has been ejected by a driver from a driver unit and has penetrated through sheets of paper, the driver unit containing a number of staples and having the driver for ejecting the staples toward the sheets of paper, thereby to clinch the staple leg on a back face side of the sheets of paper, characterized in that a plurality of projected lines adapted to be engaged with the staple leg are provided in parallel with one another, on a face of the clincher device to be engaged with the staple leg thereby to guide the staple leg inwardly, so that the staple leg can be guided inwardly by the projected lines.

Moreover, the clincher device is characterized in that the clincher device includes an inclined face which is provided on a table for supporting the sheets of paper and adapted to be engaged with the staple legs thereby to bend the staple leg inwardly, and a movable clincher member driven from a lower position to an upper position to make the staple leg which has been inwardly bent by the inclined faces to be engaged with a pressing face thereby to clinch the staple legs along the back face of the sheets of paper, wherein a plurality of projected lines adapted to be engaged with the staple leg are provided on the inclined face, so that the staple leg can be guided inwardly by the projected lines.

Further, the clincher device is characterized in that the clincher device includes inclined faces which are provided on a table for supporting the sheets of paper and adapted to be engaged with the staple leg thereby to bend the staple legs inwardly, and a movable clincher member driven from a lower position to an upper position for making the staple leg which has been inwardly bent by the inclined face engaged with a pressing face thereby to clinch the staple leg along the back face of the sheets of paper, wherein a plurality of projected lines adapted to be engaged with the staple leg are provided on the pressing face of the clincher member in parallel with one another, so that the staple leg can be guided inwardly by the projected lines.

Still further, the clincher device is characterized in that the clincher device includes clincher groove for guiding tip end of the staple leg inwardly, which is provided on an upper face of the table for supporting the sheets of paper, wherein a plurality of projected lines adapted to be engaged with the staple leg are provided on bottom faces of the clincher groove in parallel with one another, so that the staple leg can be guided inwardly by the projected lines.

BRIEF DESCRIPTION OF THE DRAWINGS

FIGS. 5(a) to 5(d) show the clincher device of FIG. 1 in operation, in which FIG. 5(a) shows a state immediately after the staple legs have penetrated through the sheets of paper, FIG. 5(b) shows a state in which the staple legs have been bent by inclined faces, FIG. 5(c) shows a state in which the staple legs have been further bent by a clincher member which has been driven upwardly, and FIG. 5(d) shows a state in which stapling operation has been completed.

FIGS. 7(a) to (c) show the clincher device according to the embodiment of FIG. 6 in operation, in which FIG. 7(a) shows a state immediately after the staple legs have penetrated through the sheets of paper, FIG. 7(b) shows a state in which the staple legs have been bent by clincher grooves, and FIG. 7(c) shows a state in which stapling operation has been completed.

Figure 1:
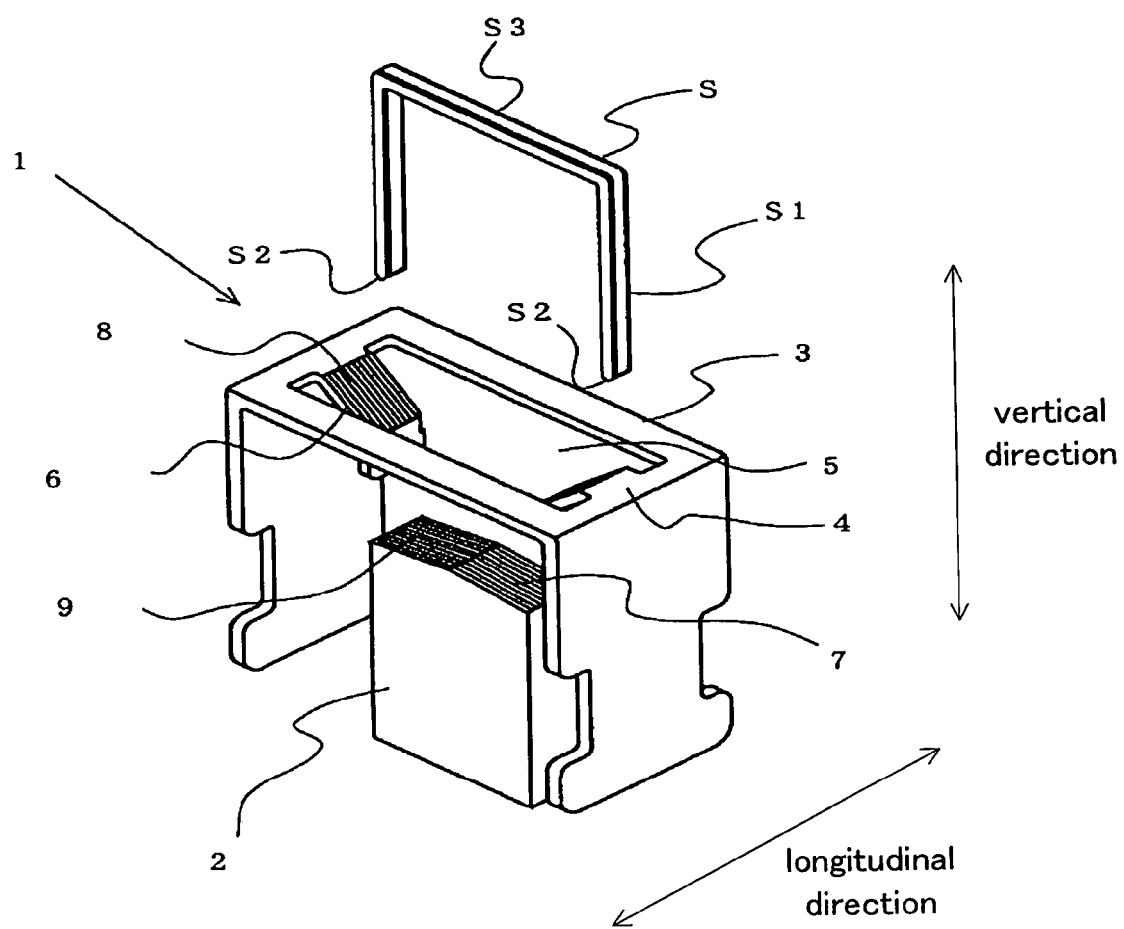
FIG. 1 is a perspective view showing a clincher device according to an embodiment of the invention.

In the drawings, designated by reference numeral 1 is a clincher device, 2 is a clincher member, 3 is a table, 4 is a receiving face, 5 is an opening, 6 is an inclined face, 7 is a pressing face, 8 is a projected line, 9 is a projected line, 10 is a driver, 11 is a clincher device, 12 is a table, 13 is a clincher groove, and 14 is a projected line.

BEST MODE FOR CARRYING OUT THE INVENTION

Now, mode for carrying out the invention will be described, referring to a first embodiment of the invention as shown in FIGS. 1 to 5. FIG. 1 shows a clincher device 1 which is provided in a clincher unit of a stapler. The clincher device 1 in this embodiment is provided with a movable clincher member 2 which is driven upwardly toward staple legs S1 which have penetrated through sheets of paper thereby to clinch the staple legs S1. The clincher device 1 is provided in a clincher unit which is so arranged as to be opposed to a driver unit which contains a number of staples S and has a driver 10 for ejecting the staple S toward the sheets of paper which is placed between the clincher unit and the driver unit. The clincher device 1 includes a table 3 which is arranged so as to be opposed to a staple ejecting part of the driver unit and adapted to clamp the sheets of paper in cooperation with the driver unit, and a clincher member 2 which is arranged so as to slide with respect to the table 3, along an ejecting direction of the staple S.

A flat receiving face 4 for receiving the sheets of paper is provided on an upper face of the table 3, and an opening 5 for receiving the staple legs S1 which have been ejected from the driver unit and penetrated through the sheets of paper is provided in a center part of the receiving face 4. The table 3 is provided, inside the opening 5 on both sides thereof, with inclined faces 6 which are inclined downwardly and inwardly from the both sides of the opening 5 and adapted to be engaged with tip ends S2 of the staple legs S1 thereby to bend both the staple legs S1 inwardly. The tip ends S2 of the staple legs S1 which have penetrated through the sheets of paper and entered into the opening 5 are respectively engaged with these inclined faces 6, and the tip ends S2 of both the staple legs S1 are guided so as to be directed inwardly to each other and bent. The inclined faces 6 have a large size in a longitudinal direction so that the tip ends S2 of the staple legs S1 which have penetrated through the sheets of paper may land on either position of the inclined faces, even in case where the driver unit and the clincher unit are somewhat deviated in position.

The clincher member 2 is disposed inside the inclined faces 6 in the opening 5 and so arranged as to slide along the ejecting direction of the staple S. The clincher member 2 is adapted to be driven from a lower position to an upper position after the staple S has been ejected, in association with action of ejecting means which ejects the staple S toward the sheets of paper by means of driving means which is not shown. On an upper end face of the clincher member 2, there is provided a pressing face 7 which can be engaged with the tip ends S2 of the staple legs S1 which have been inwardly bent by the inclined faces 6. The clincher member 2 is on standby in the lower position on ordinary occasions, so that the pressing face 7 may not get in touch with the staple legs S1 until the staple legs S1 have completely penetrated through the sheets of paper. After the staple legs S1 have completely penetrated through the sheets of paper, the clincher member 2 is driven upwardly, and the pressing face 7 is engaged with the tip ends S2 of the staple legs S which have been bent inwardly by the inclined faces 6, thereby to push the staple legs S1 until they strike a back face of the sheets of paper. Then, the staple legs S1 are clinched along the back face of the sheets of paper to conduct stapling action.

Figure 4:
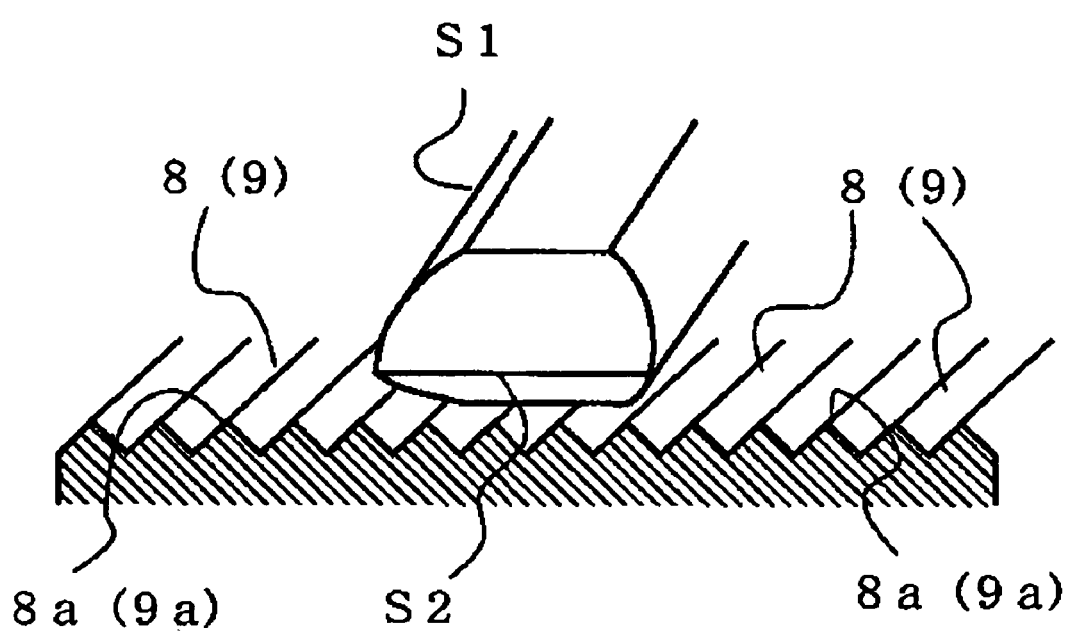
FIG. 4 is a sectional view showing a tip end of a staple leg in a state engaged with projected lines.

The inclined faces 6 provided on the table 3 are provided with a plurality of projected lines 8 along an inclination direction of the inclined faces 6, in parallel with one another. As shown in FIG. 4, the projected lines 8 are provided by cutting work or grinding work so as to form pointed edges 8a on their tops having a height of about 0.1 mm to a few micron. When the tip ends S2 of the staple legs S1 which have been engaged with the inclined faces 6 are engaged with the tops of the projected lines 8, the pointed edges 8a of the projected lines 8 bite the tip ends S2 of the staple leg S1 thereby to guide the staple legs S1 along the projected lines 8. An interval between the adjacent projected lines 8 is preferably set corresponding to a width of a linear material of the staple legs S1 so that the two or more edges 8a of the projected lines are simultaneously engaged with one of the tip ends S2 of the staple legs S1.

The pressing face 7 of the clincher member 2 is also provided with a plurality of projected lines 9 extending substantially in parallel with a crown part S3 of the staple S. The projected lines 9 are adapted to guide the tip ends S2 of the staple legs S1 which are engaged with the pressing face 7 when the clincher member 2 is driven upwardly. In this manner, the projected lines 8, 9 are respectively provided on the inclined faces 6 of the table 3 and on the pressing face 7 of the clincher member 2, and accordingly, friction coefficient of the staple leg S1 engaged with these projected lines 8, 9 is made to be extremely larger in a longitudinal direction than in a vertical direction. Therefore, the staple leg S1 will be prevented from moving in the longitudinal direction. Consequently, the tip ends S2 of the staple legs S1 which have penetrated through the sheets of paper and have been engaged with the inclined faces 6 will be guided along the projected lines 8 provided on the inclined faces 6, and thereafter, the tip ends S2 of the staple legs S1 will be engaged with the projected lines 9 provided on the pressing face 7 of the clincher member 2 thereby to be guided along the direction of the projected lines 9. As the results, the staple legs S1 are clinched in a direction substantially parallel to the crown part S3 of the staple S.

Figure 2:
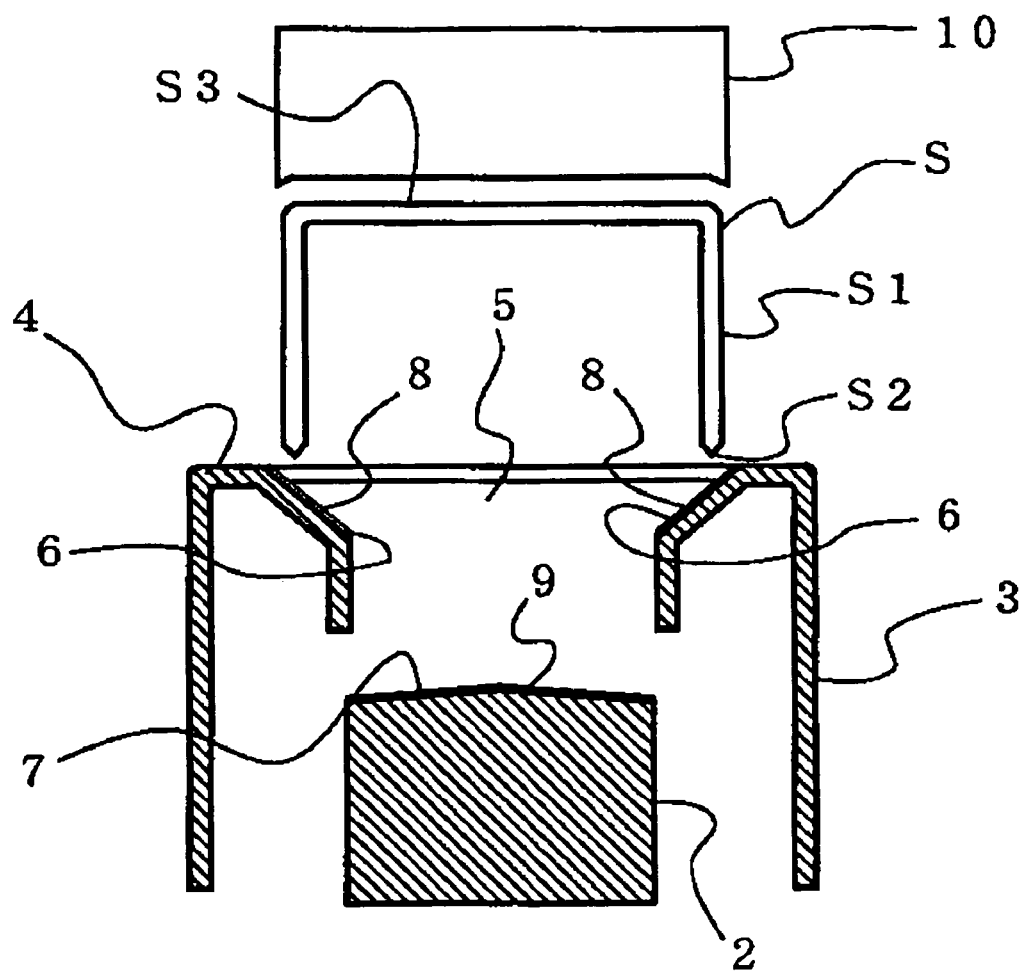
FIG. 2 is a front view, in vertical section, of the clincher device according to the embodiment of the invention.
Figure 3:
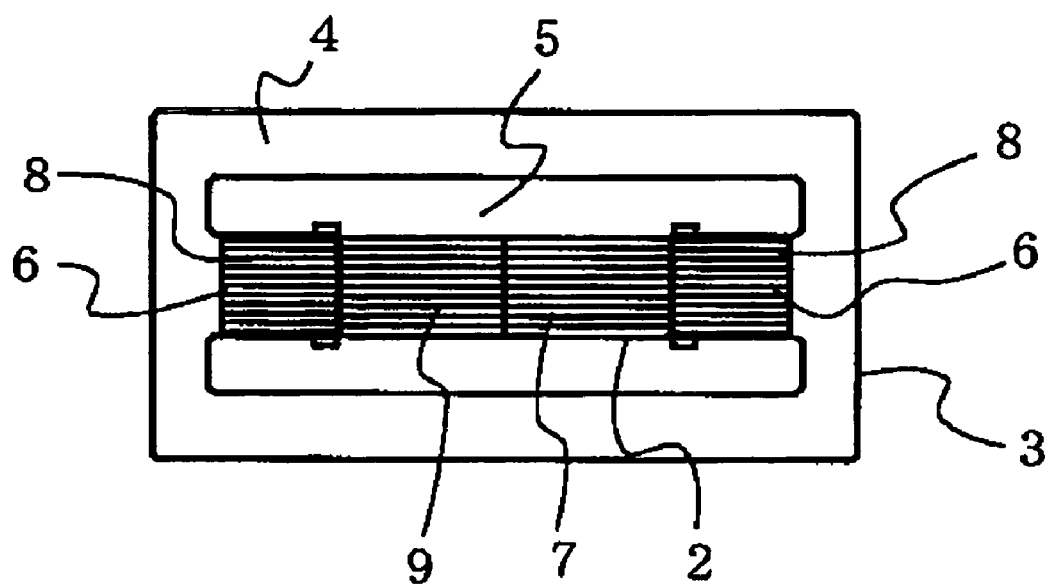
FIG. 3 is a plan view of the clincher device according to the embodiment of the invention.
Figure 5A:
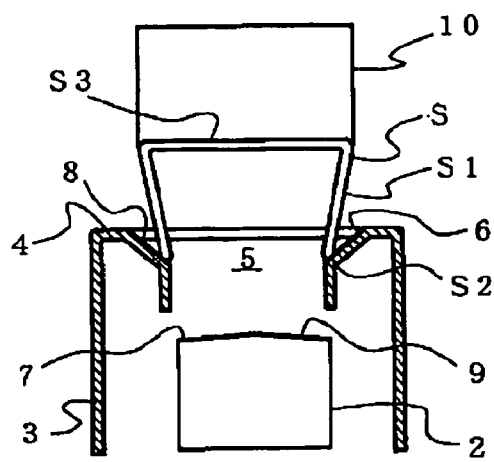

Stapling operation of the staple S according to this embodiment will be described referring to FIGS. 2 and 5. As shown in FIG. 2, when the driver 10 of the driver unit is actuated, the staple S loaded in the driver unit will be ejected toward the sheets of paper. Then, the tip ends S2 of the staple legs S1 will pass through the sheets of paper placed on the upper face of the table 3 which is provided on the clincher unit, and enter into the opening 5 of the table 3, whereby the tip ends S2 of the staple legs S1 will be engaged with the inclined faces 6 which are provided on both sides of the opening 5 of the table 3. As shown in FIG. 5(a), as the ejection of the staple S by the driver 10 proceeds, the staple legs S1 will be guided along the inclined faces 6 and bent inwardly toward each other. On this occasion, the edges 8a of the projected lines 8 provided on the inclined faces 6 will bite the tip ends S2 of the staple legs S1 to guide the tip ends S2 of the staple legs S1 along the projected lines 8. Therefore, the tip ends S2 of the staple legs S1 will not move in a longitudinal direction, and leaning of the staple will not happen.

Figure 5B:
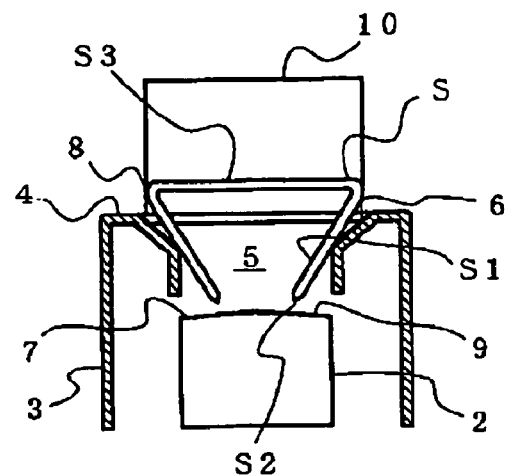
Figure 5C:
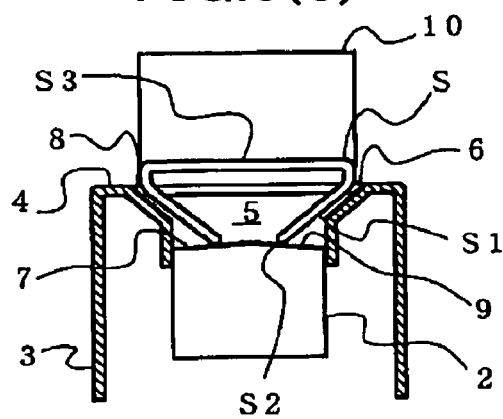

As shown in FIG. 5(b), when the staple legs S1 have completely penetrated through the sheets of paper, the tip ends S2 of the staple legs S1 have been pushed beyond lower ends of the inclined faces 6 to be further bent inwardly. Thereafter, the clincher member 2 will be driven from the lower position to the upper position by means of a driving mechanism which is provided in the clincher unit. As shown in FIG. 5(c), the pressing face 7 of the clincher member 2 will be engaged with the tip ends S2 of the staple legs S1, and will clinch the staple legs S1 so as to press them onto the back face of the sheets of paper. On this occasion, the tip ends S2 of the staple legs S1 will be pressed with the pressing face 7 of the clincher member 2, and the edges 9a of the projected lines 9 provided on the pressing face 7 of the clincher member 2 will bite the tip ends S2 of the staple legs S1, thereby to guide the staple legs S1 so as to be in parallel with the crown part S3 of the staple, preventing the tip ends S2 of the staple legs S1 from moving in the longitudinal direction.

Figure 5D:
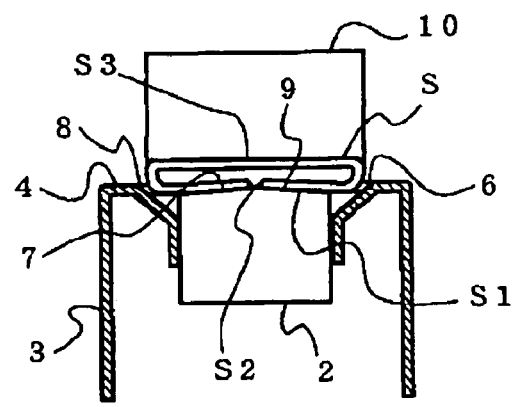

Further, as shown in FIG. 5(d), the clincher member 2 will be further driven upwardly until the pressing face 7 gets in touch with the back face of the sheets of paper, and will clinch the staple legs S1 along the back face of the sheets of paper to conduct the stapling action. On this occasion, the tip ends S2 of the staple legs S1 will be engaged with the projected lines 9 provided on the pressing face 7 of the clincher member 2 which has been driven to the upper position, whereby lateral movement of the staple legs S1 will be restricted, and both the legs S1 will be clinched into a shape in parallel with the crown part S3 of the staple S.

In the above embodiment, the projected lines 8, 9 which are respectively provided on the inclined faces 6 provided in the opening 5 of the table 3 and the pressing face 7 of the clincher member 2 are provided so as to be in parallel with a lateral direction of the crown part S3 of the staple S. However, in case where the direction of the projected lines 8, 9 is slightly oriented with respect to the lateral direction of the crown part S3 of the staple S, it would be possible to clinch the legs S1 in a bypass clinching manner, which will prevent from crossing of both the legs S1 when the staple S having rather long legs S1 is used. Moreover, although, in the above embodiment, the projected lines 8, 9 are respectively provided on the inclined faces 6 provided in the opening 5 of the table 3 and the pressing face 7 of the clincher member 2, the projected lines may be provided on either of the inclined faces 6 of the table 3 and the pressing face 7 of the clincher member 2.

Then, referring to FIG. 6, another embodiment of the invention will be described. In the foregoing embodiment, the invention has been applied to the clincher device 1 provided with the movable clincher member 2 which is driven upwardly toward the staple legs S1 which have penetrated through the sheets of paper, thereby to clinch the staple legs S1. However, a clincher device 11 in this embodiment has clincher grooves 13 provided on a table 12 which is provided in the clincher unit opposed to the driver unit for the sheets of paper to be placed thereon. The clincher grooves 13 are adapted to be engaged with the staple legs S1 which have penetrated through the sheets of paper and projected to the back face side of the sheets of paper, thereby to bend the staple legs S1 inwardly.

Figure 6:
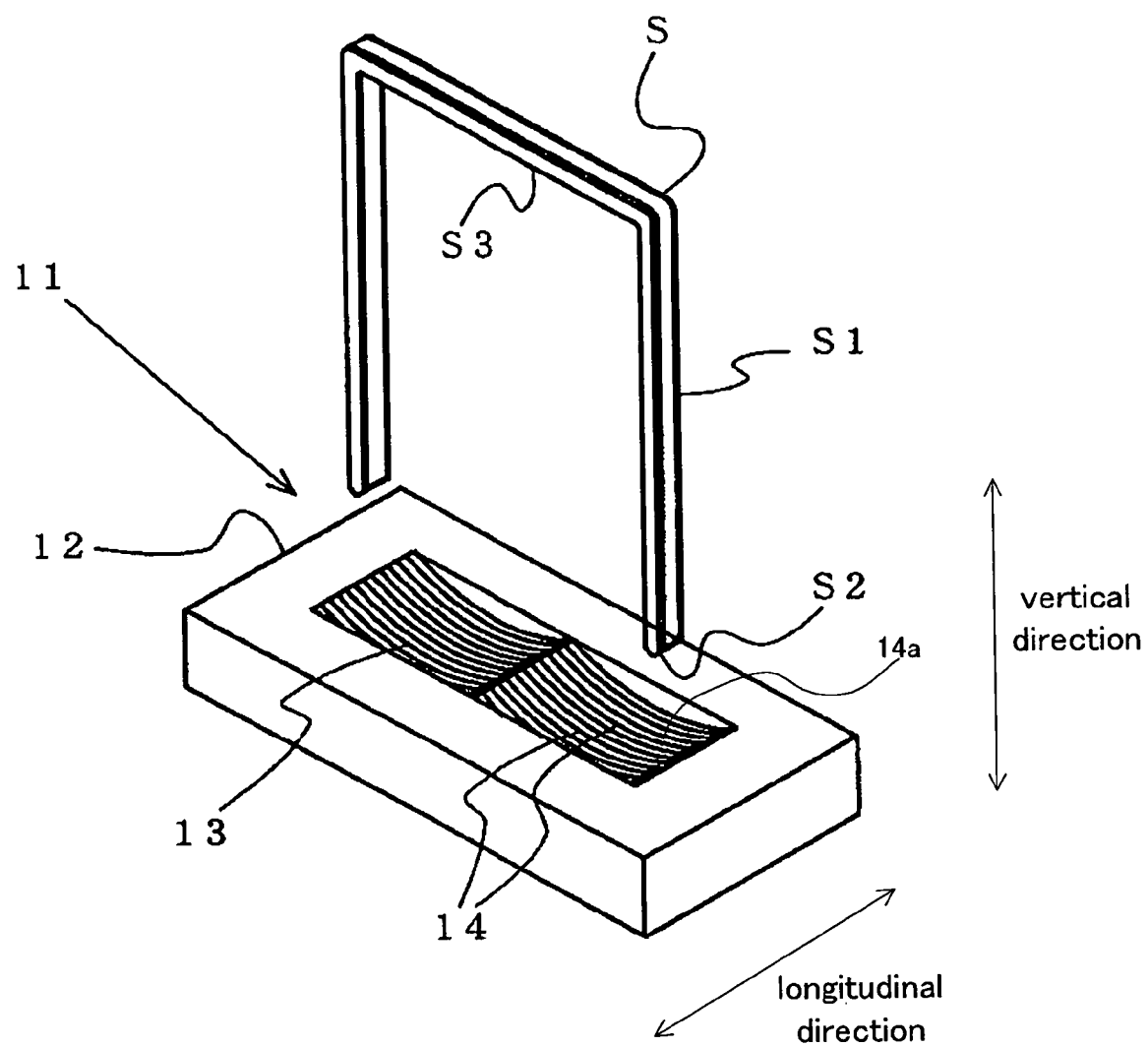
FIG. 6 is a perspective view showing a clincher device according to another embodiment of the invention.

As shown in FIG. 6, the clincher grooves 13 which are adapted to be engaged with the tip ends S2 of the staple legs S1 so as to inwardly guide the staple legs S1 are provided on an upper face of the table 12 provided in the clincher unit. In usual cases, these clincher grooves 13 are provided having a small width in a longitudinal direction which is substantially same as a width of the linear material of the staple S. However, in this embodiment, the clincher grooves 13 are provided having a considerably larger width than the width of the linear material of the staple S, so that the tip ends S2 of the staple legs S1 can make a reliable landing in the clincher grooves 13, even though a slight positional deviation has occurred between the clincher unit and the driver unit.

The clincher grooves 13 are provided, on their bottom faces, with a plurality of projected lines 14 which extend along a direction of the clincher grooves 13 in parallel with one another. The projected lines 14 have pointed edges 14a which are continuously provided on their tops by cutting or grinding, as in the foregoing embodiment. The pointed edges 14a of the projected lines 14 are engaged with the staple legs S1 thereby to bite the staple legs S1, and the staple legs S1 will be guided along the projected lines 14.

Figure 7A:
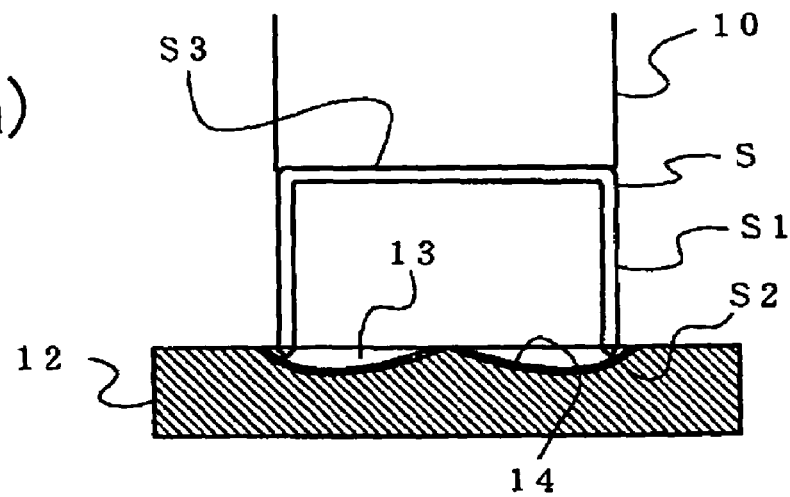
Figure 7B:
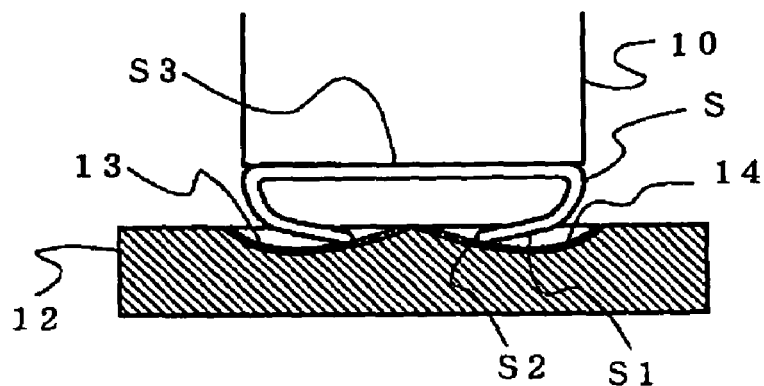
Figure 7C:
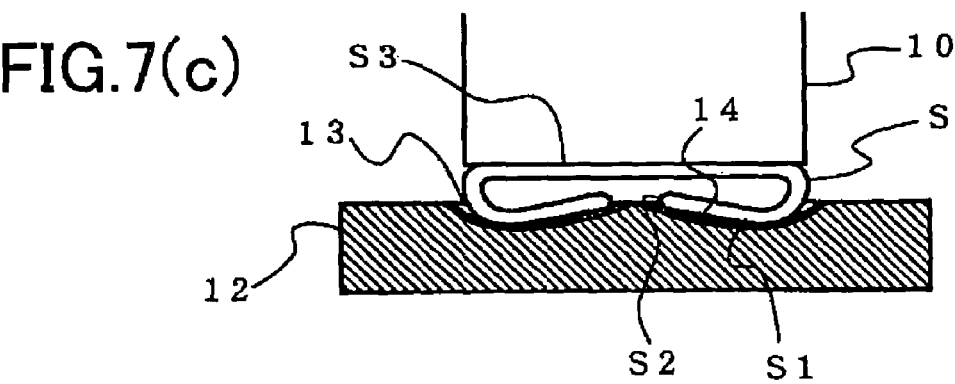
Figure 8:
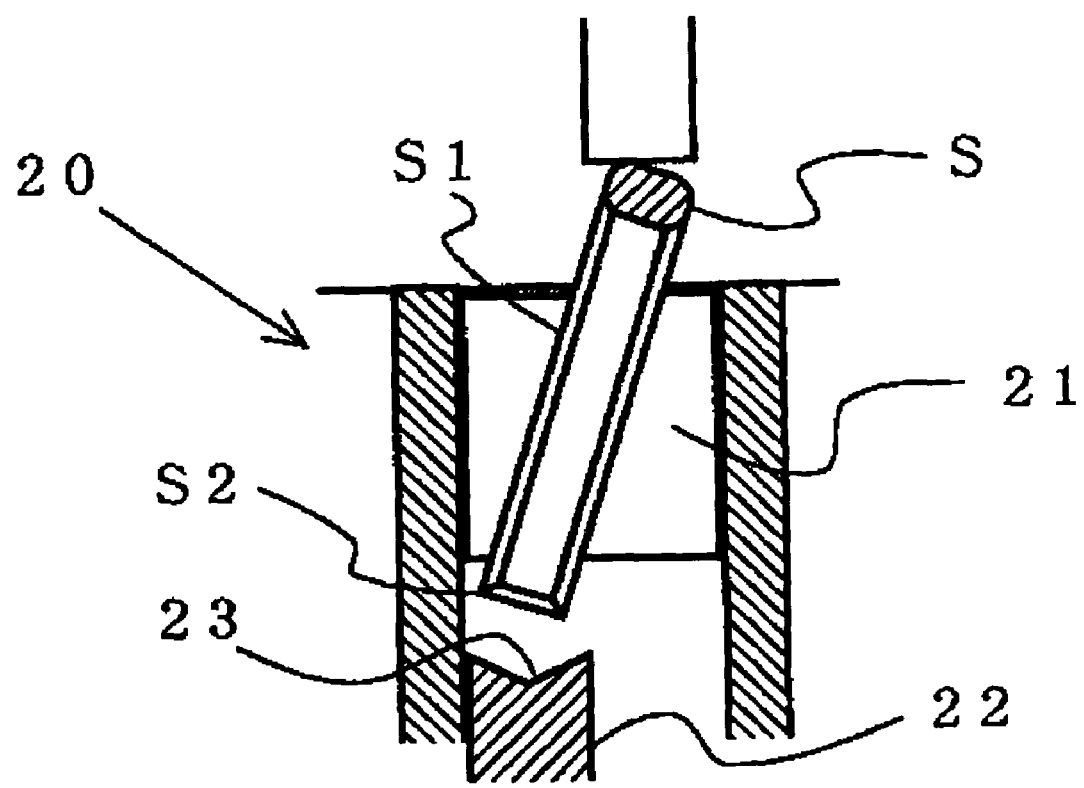
FIG. 8 is a side view, in vertical section, showing a conventional clincher device in operation.
Figure 9:
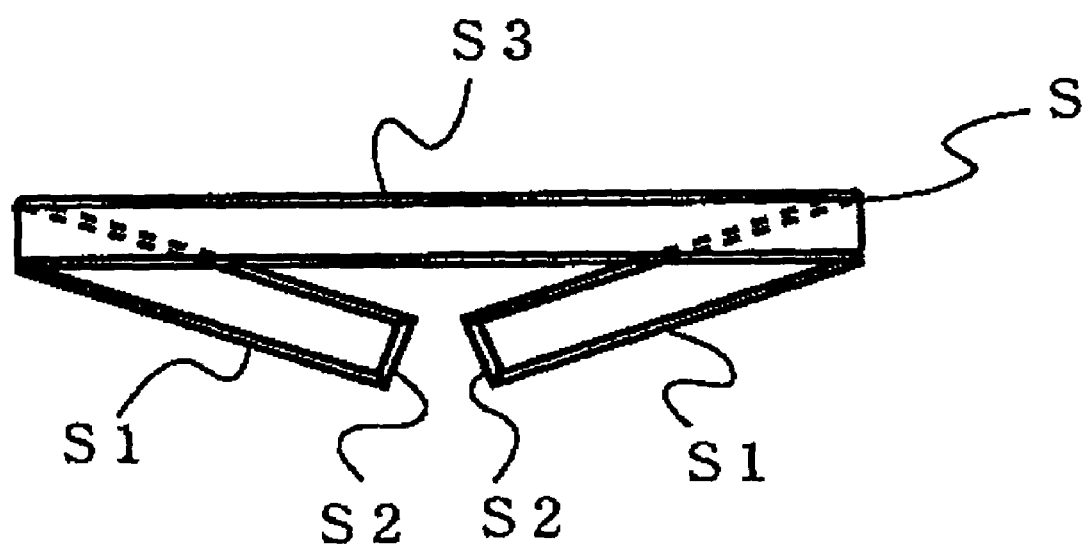
FIG. 9 is a plan view of the staple which has been clinched by the conventional clincher device.

Then, referring to FIGS. 7(a) to 7(c), operation of the above embodiment for binding the sheets of paper will be described. As shown in FIG. 7(a), the tip ends S2 of the staple legs S1 which have been ejected by the driver 10 of the driver unit and penetrated through the sheets of paper will land on the clincher grooves 13 provided on the table 12. The driver 10 continues to push the staple S, and as shown in FIG. 7(b), the tip ends S2 of the staple legs S1 will be guided by the clincher grooves 13 and inwardly bent. On this occasion, the edges 14a provided on the tops of the projected lines 14 will bite the tip ends S2 of the staple legs S1 for restricting longitudinal movement of the staple legs S, and the staple legs S1 will be guided along the edges 14a of the projected lines 14 to be clinched into a state substantially in parallel with the crown part S3 of the staple S. As the driver 10 further continues to push the staple S, the crown part S3 of the staple S which is engaged with the driver 10 will be pressed so as to be brought into tight contact with the upper face of the sheets of paper, and the staple legs S1 will be clinched by the clincher grooves 13 so as to be brought into tight contact with the back face of the sheets of paper, as shown in FIG. 7(c). In this manner, the stapling operation is completed.

INDUSTRIAL APPLICABILITY

As described above, according to the clincher device of the stapler in this invention, a plurality of the projected lines to be engaged with the staple legs are provided in parallel with one another, on the face of the clincher device which is adapted to be engaged with the staple for guiding the staple legs inwardly. Therefore, when the tip ends of the staple legs are engaged with the projected lines, frictional resistance in the longitudinal direction will be increased, so that the longitudinal movement of the staple legs may be restricted, and the staple legs will be guided along the direction of the projected lines and clinched. As the results, even though the clincher device has a large size in the longitudinal direction, leaning or so of the staple will not happen, and the staple legs will be clinched in a state substantially in parallel with the crown part. Accordingly, allowance in size for positional alignment between the driver unit and the clincher unit can be set larger, and it is possible to reduce the time required for adjustment or so.

Moreover, the clincher device includes the inclined faces which are provided on the table for supporting the sheets of paper and adapted to be engaged with the staple legs thereby to bend the staple legs inwardly, and the movable clincher member having the pressing face adapted to be engaged with the staple legs which have been inwardly bent by the inclined faces, when the movable clincher member is driven from the lower position to the upper position, thereby to clinch the staple legs along the back face of the sheets of paper, wherein a plurality of the projected lines are provided on the inclined faces. Therefore, when the tip ends of the staple legs are engaged with the projected lines, frictional resistance in the longitudinal direction will be increased so that the longitudinal movement of the staple legs may be restricted, and the staple legs will be guided along the direction of the projected lines and clinched. As the results, even though the clincher device has a large size in the longitudinal direction, leaning or so of the staple will not happen, and the staple legs will be clinched in a state substantially in parallel with the crown part. Accordingly, allowance in size for positional alignment between the driver unit and the clincher unit can be set larger, and it is possible to reduce the time required for adjustment or so.

Further, the clincher device includes the inclined faces which are provided on the table for supporting the sheets of paper and adapted to be engaged with the staple legs thereby to bend the staple legs inwardly, and the movable clincher member having the pressing face adapted to be engaged with the staple legs which have been inwardly bent by the inclined faces, when the movable clincher member is driven from the lower position to the upper position, thereby to clinch the staple legs along the back face of the sheets of paper, wherein a plurality of the projected lines are provided on the pressing face of the clincher member. Therefore, when the tip ends of the staple legs are engaged with the projected lines provided on the pressing face of the clincher member, frictional resistance in the longitudinal direction will be increased so that the longitudinal movement of the staple legs may be restricted, and the staple legs will be guided along the direction of the projected lines and clinched. As the results, even though the clincher device has a large size in the longitudinal direction, leaning or so of the staple will not happen, and the staple legs will be clinched in a state substantially in parallel with the crown part. Accordingly, allowance in size for positional alignment between the driver unit and the clincher unit can be set larger, and it is possible to reduce the time required for adjustment or so.

Still further, the clincher device includes the clincher grooves which are provided on the table for supporting the sheets of paper and adapted to guide the tip ends of the staple legs inwardly, and a plurality of the projected lines are provided on the bottom faces of the clincher grooves. Therefore, when the tip ends of the staple legs are engaged with the projected lines, frictional resistance in the longitudinal direction will be increased so that the longitudinal movement of the staple legs may be restricted, and the staple legs will be guided along the direction of the projected lines and clinched. As the results, even though the clincher device has a large size in the longitudinal direction, leaning or so of the staple will not happen, and the staple legs will be clinched in a state substantially in parallel with the crown part.

The invention claimed is:

1. A clincher device of a stapler for engaging with a staple leg ejected by a driver and penetrated through sheets of paper so as to clinch the staple leg on a back face side of the sheets of paper, comprising:
    a plurality of projected lines on a face for engaging with the staple leg and inwardly guiding the staple leg, the plurality of projected lines being formed in parallel with one another;
    wherein each of the plurality of the projected lines comprises a pointed edge on a top of the each of the plurality of the projected lines; and
    a tip end of the staple leg simultaneously engages with at least two of the pointed edges.

2. The clincher device of a stapler according to claim 1, further comprising:
    an inclined face, provided on a table for supporting the sheets of paper, for engaging with the staple leg and inwardly bending the staple leg; and
    a movable clincher member, having a pressing face for engaging with the staple leg inwardly bent by the inclined faces, for clinching the staple leg along the back face of the sheets of paper by driving the movable clincher member from a lower position to an upper position,
    wherein the plurality of the projected lines are provided on the inclined face.

3. The clincher device of a stapler according to claim 1, further comprising:
    an inclined face, provided on a table for supporting the sheets of paper, for engaging with the staple leg and inwardly bending the staple leg; and
    a movable clincher member, having a pressing face for engaging with the staple leg inwardly bent by the inclined faces, for clinching the staple leg along the back face of the sheets of paper by driving the movable clincher member from a lower position to an upper position,
    wherein the plurality of the projected lines are provided on the pressing face.

4. The clincher device of a stapler according to claim 1, further comprising:
    an inclined face, provided on a table for supporting the sheets of paper, for engaging with the staple leg and inwardly bending the staple leg; and
    a movable clincher member, having a pressing face for engaging with the staple leg inwardly bent by the inclined faces, for clinching the staple leg along the back face of the sheets of paper by driving the movable clincher member from a lower position to an upper position, wherein the plurality of the projected lines are provided on both the inclined face and the pressing face.

5. The clincher device of a stapler according to claim 1, further comprising:

a clincher groove, provided on a table for supporting the sheets of paper, for inwardly guiding a tip end of the staple leg, wherein the plurality of the projected lines are provided on bottom faces of the clincher groove.

* * * * *